United States Patent [19]  [11] 4,355,175
Pusztaszeri  [45] Oct. 19, 1982

[54] METHOD FOR RECOVERY OF TEREPHTHALIC ACID FROM POLYESTER SCRAP

[76] Inventor: Stephen F. Pusztaszeri, 14 Clark Pl., Port Chester, N.Y. 10573

[21] Appl. No.: 251,499

[22] Filed: Apr. 6, 1981

[51] Int. Cl.³ .................. C07C 51/00; C07C 51/42; C07C 27/26
[52] U.S. Cl. .................................. 562/483; 562/485; 568/868; 568/871
[58] Field of Search ............... 562/483, 485; 568/868, 568/871

[56] References Cited

FOREIGN PATENT DOCUMENTS 523222  3/1956  Canada .................. 562/483

Primary Examiner—Alan Siegel
Attorney, Agent, or Firm—Florence U. Reynolds

[57] ABSTRACT

Polyester scrap such as film (plain or silver-bearing), fabric, yarn or bottles, based primarily on polyethylene terephthalate, is depolymerized at room temperature and atmospheric pressure with a mixture of concentrated sulfuric acid and water to form crude terephthalic acid which is purified by dissolving in alkali solution, filtering to remove impurities, acidifying the filtrate to recover terephthalic acid in high yield with a purity of at least 99%.

11 Claims, No Drawings

METHOD FOR RECOVERY OF TEREPHTHALIC ACID FROM POLYESTER SCRAP

BACKGROUND OF THE INVENTION

This invention relates to an economical process for recovery of terephthalic acid (TPA) from various polyester waste materials.

The extensive use of polyesters and the need for disposal of polyester waste has created a great problem for many industries. In the past, polyester waste has often been used for landfills or has been incinerated because there was no economical recovery process available or the contaminants caused severe difficulties in its reapplication.

Various processes have been proposed for the recovery of TPA from various waste materials but they are very expensive, often incomplete and some release undesirable gases which pollute the atmosphere and, in general, they have not enjoyed commercial success. The most common way is to depolymerize the polyester with alkali as shown in U.S. Pat. Nos. 3,953,502 and 3,956,088.

It is the main object of this invention to provide an economical and industrially feasible process for processing all kinds of polyethylene terephthalate (PET) type waste material and for obtaining marketable TPA at low cost with substantially complete recovery.

It is intended to deal solely with solid waste material in large volumes regardless of its main origin. The solid waste scrap materials can be classified into four groups.
1. Silver-bearing films (X-ray film, exposed/non-exposed films and microfilms)
2. Regular films (non-photographic, with or without another plastic coating)
3. Textiles (crude polymer, yarn and fabrics)
4. Bottles (clear or colored)

A general procedure is submitted herewith but is not limited as representative of a process embodying the features of this invention.

SUMMARY OF THE INVENTION

Briefly described, the general procedure in accordance with the practice of this invention comprises the following steps:

Step 1

The PET scrap (chips, granules, compressed or in any convenient form) is placed into a vessel which is corrosion resistant (glass lined or hevac type) equipped with sufficient agitation and with a heater. Sufficient water and concentrated sulfuric acid in a volume ratio of 2 to 8.5-13 are added under constant mixing, at atmospheric pressure and room temperature. Heat is applied in a cold climate, if necessary. Within 5 to 30 minutes under constant mixing the solid waste materials will be completely liquified (depolymerized). They are then diluted with an equal volume of cold water. The diluted liquid is then rapidly filtered.

The solid material is collected in the filter, the liquid material (ethylene glycol; water; excess acid and some impurities) is discarded (waste disposed).

Step 2

The collected solids, containing the TPA and impurities, are suspended in water in a convenient tank at room temperature, then treated with potassium, ammonium or sodium hydroxide, to raise the pH to 6 to 13. In this step the TPA will dissolve and the impurities will be precipitated. The solution may be dark brown-black in color, depending on the amount of impurities and the pH. The lower pH range avoids the formation of fine precipitate which results from decomposition of any vinylidene chloride present on some films. Thus it is easier to filter but the yield of acid recovered is the same. After filtration to remove the fine precipitate, the residue (undissolved scrap material, if any, and impurities) is discarded as solid waste. The liquid is then collected and must be clear, although it may be light brownish in color (if dark colored, it must be treated with activated charcoal and refiltered from the charcoal). The obtained solution is then acidified with diluted or concentrated sulfuric acid to a pH of 0-2 to cause precipitation of TPA.

Step 3

The TPA is filtered and washed with water until acid- and salt-free. The washed TPA is then dried, preferably at 105°-110° C. (electric, gas or hot air dryer) to constant weight, then ground or pulverized and packed.

The following reactions occur during the recovery process.

Step 1

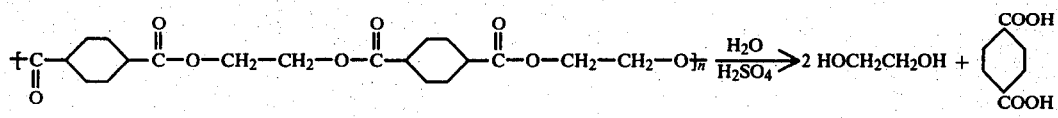

Step 2

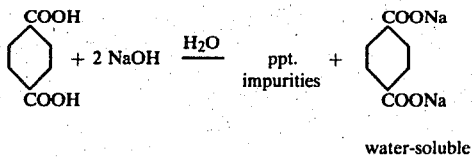

Step 3

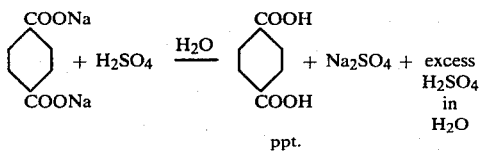

DETAILED DESCRIPTION

The following examples will clearly show the feasibility of the process.

For TPA recovery from silver-bearing polyester film scrap, the silver is removed from the polyester type base by any known process. The silver-free and dry weighed scrap film (chips, granules or any other form) contains not less than 98% of polyester scrap. The other 2% can be a coating (vinylidene chloride), paper, acetate base scrap but no metals of any kind. The scrap film is charged into an open or closed chemical vessel, which is equipped with a heater and mixing means and is corrosion resistant. The size of all equipment is directly proportional to the volume. After the vessel is charged with the scrap, water and concentrated sulfuric acid are pumped in with constant mixing. Within 5 to 30 minutes at room temperature and atmospheric pressure, the solid waste material depolymerizes (is liquified). The depolymerization, reaction is exothermic. After depolymerization, the volume is doubled with cold water, then the liquid is filtered and all solids collected on the filter. The filtrate is discarded. The empty vessel is then ready for the next batch.

The collected solid material from the filter is suspended in water in a suitable tank under constant agitation, neutralized with an alkali hydroxide (solid KOH, NaOH or concentrated $NH_4OH$) and the pH of the solution adjusted to between 6–13. Lithium hydroxide could be used but it is too expensive for economical recovery. The hydroxides of calcium, barium, magnesium, or strontium could also be used but complications may arise because of their double valency or the formation of sulfates.

The obtained solution which is brown colored, is then filtered on a fine filter to remove all undissolved materials (vinylidene chloride polymer, small amounts of undissolved film chips and other impurities) or precipitated materials. The obtained solids constitute the only solid waste material. The filtrate, which must be completely clear and light yellow-brownish in color (if the solution is very dark in color, activated charcoal filtration is required) is acidified with sulfuric acid (concentrated or diluted) and the acidity of the solution adjusted to about pH 0–2 to insure total precipitation of the terephthalic acid which is then filtered and washed acid- and salt-free with cold water.

The clean acid is then dried, preferably at 105° C. and ground and packed in lined (plastic) bags or drums.

EXAMPLE 1

A sample of scrap was used which contained a large amount of silver (over 5% by wt.) but having a 100% PET base.

An 11 gram sample was first treated at room temperature with 50 ml. dilute nitric acid to remove the silver. Then the dilute acid was removed and the film chips were washed with 2×25 ml cold water. This is a pretreatment for the above scrap and not part of the present invention.

10 g of the dried silver-free scrap was then treated with 2.0 ml water and 11.0 ml concentrated sulfuric acid (95–97% pure) at atmospheric pressure and room temperature. The resins were depolymerized in 2–5 minutes, then the reaction mixture was diluted with 13.0 ml cold water under constant agitation and then filtered. The obtained liquid was clear and was discarded.

The obtained precipitate was then suspended in 50 ml water and 9 g of 85% KOH was added to dissolve the crude TPA and to precipitate the impurities at an elevated pH of 11–13. A dark brown precipitate formed in the solution indicating that the impurities had reacted. The solution mixture was then filtered through a fine filter which is capable of removing all the precipitate and undissolved particles. This is very important. The clear, yellowish-brown filtrate was acidified with 9 ml of conc. $H_2SO_4$ to obtain a solution having a pH of 2 and to precipitate TPA. The obtained solid TPA was then filtered, washed with cold water until acid- and salt-free ($K_2SO_4$). The clean acid was dried at 105° C. The dried TPA weight was 7.56 g or 75.6% yield. It was white in color and better than 99% pure.

$$\% \text{ Yield} = \frac{\text{Calculation of Yield}}{\frac{(\text{weight of TPA obtained}) \times 100}{(\text{weight of scrap} - (\text{residue, if sample}) \quad \text{lg. amount})}}$$

If the impurities in the scrap material amount to more than 2% (paper, acetate base or other), the weight of the precipitate after the alkali treatment and filtration must be determined by drying to constant weight at 105° C. and the scrap sample weight must be corrected.

EXAMPLE 2

100 g of clean silver-bearing polyester waste chips containing less than 3% silver impurities, were treated with 20 ml water and 110 ml conc. sulfuric acid and the procedure of Example 1 was followed. The obtained TPA weighed 82.56 g, representing an 82.56% yield.

EXAMPLE 3

1000 g of a clean silver-bearing sample containing less than 3% silver impurities, was treated with 200 ml water and 1100 ml conc. sulfuric acid and the procedure of Example 1 was followed. The obtained TPA weighed 759.25 g, representing a 75.93% yield.

EXAMPLE 4

A silver-bearing type scrap material which contained 3.5% silver and a large amount of acetate base (10%) impurities was used.

100 g of the above sample was treated with 20 ml water and 110 ml concentrated sulfuric acid and the procedure of Example 1 was followed. The obtained TPA weighed 65.5 g, representing a 65.5% yield. The residue weighed 10.1 g. The corrected yield was 72.8%.

The following Examples 5-1 to 5-6 illustrate the amount of acid required to depolymerize the scrap material in reasonable time and with no additional heat. The room temperature was 25° C. and atmospheric pressure was used. In each case the sample weight was 100 g. All chips were silver-free, 100% PET base, previously dried to constant weight. All chemicals were analytical grade. The purity of the obtained acid was better than 99% as compared with pure analytical grade TPA. Only the yield, not the purity, of the TPA is effected if less acid is used as in Ex. 5-1 and 5-2. The results are shown in the following table.

| Ex. | ml H$_2$O | ml conc. H$_2$SO$_4$ | Time (min) | TPA yield in g |
|---|---|---|---|---|
| 5-1 | 20 | 85 | 30 | 77.3 |
| 5-2 | 20 | 90 | 25 | 77.7 |
| 5-3 | 20 | 100 | 15 | 78.0 |
| 5-4 | 20 | 110 | 5 | 78.0 |
| 5-5 | 20 | 120 | 5 | 78.0 |
| 5-6 | 20 | 130 | 5 | 78.5 |

The above experiments clearly show that if not enough acid is used, more time is required to depolymerize the materials. If heat is applied, the time can be shortened but the economy of the process will be offset. If the time is kept constant, the sample will not depolymerize and good TPA recovery is not obtained. The best results were obtained when 110 ml conc. sulfuric acid were used with 20 ml water. Thus, the preferred volume ratio of acid to water is 11 to 2, but a ratio of 8.5-13 to 2 gives good results.

EXAMPLE 6

The material used was non-silver-bearing PET film scrap of light blue color.

1000 g. of the scrap film, originally from a 60 inch wide roll) was cut into small pieces, put into a container which contained 200 ml water and 1100 ml conc. sulfuric acid. Under constant stirring the film was depolymerized at room temperature and atmospheric pressure within 5 minutes. After depolymerization, the mixture was diluted with 1300 ml cold water and then filtered. The filtrate was discarded. The solid material from the filter was suspended in water and then alkali was added to elevate the pH to 11 under constant mixing. The solution was filtered, and the clear liquid was acidified with sulfuric acid to pH 0-3. The precipitated TPA was filtered, washed acid- and salt-free with cold water to neutral pH and dried at 105° C. The obtained TPA weighed 829.70 g corresponding to 82.97% yield.

Note: The above scrap material contained only 0.5 to 1.5% by weight of a vinylidene chloride polymer coating and a very small amount (0.2%) of a blue dye as impurities.

EXAMPLE 7a

The material used was textile scrap.

100 g of scrap was put into a container which contained 20 ml water and 100 ml of conc. sulfuric acid. Under constant agitation the material was depolymerized within 10 min. The solution was then diluted with an equal volume (120 ml) of cold water and then filtered. The solid material was suspended in water and neutralized with NaOH. The resulting solution was very dark colored but clear. 30 g of activated charcoal was added and the mixture filtered. The resulting solution was clear and very light in color (yellowish-brown). This solution was acidified to pH 2 and the precipitated TPA was filtered off and washed. The dried TPA was white and weighed 73.75 g, representing a 73.75% yield.

EXAMPLE 7b

The material used was polyester scrap yarn or crude fabric containing some oil as a protective agent.

100 g of yarn was put into a container which contained 20 ml water and 100 ml conc. sulfuric acid. The yarn very rapidly depolymerized under constant stirring. The solution was diluted with 120 ml water and then filtered. The solid material from the filter was dispersed in water and then neutralized with KOH to a pH between 10 and 13. The alkaline solution was filtered to yield a very light yellowish colored clear filtrate. This was acidified with 20 ml conc. sulfuric acid to precipitate TPA. The TPA was filtered and washed acid- and salt-free and then dried at 105° C. The dried TPA weight of 84.35 g, corresponded to an 84.35% yield.

Note: The TPA obtained from textile yarn (staple or monofilament) has the highest purity, 99.6 or better.

EXAMPLE 8

A previously used polyester beverage bottle was separated from the metal cap and the polyethylene reinforcement bottom part. The remainder was crushed to a small size to reduce the volume. The crushed bottle scrap contained paper from the label and glue, as well as a little dye as impurities.

100 g of the crushed scrap was put into a container which contained 25 ml water and 130 ml conc. sulfuric acid. Under constant mixing at room temperature, the material was depolymerized within 10 min. The mixture was diluted with 160 ml cold water and then filtered.

The filtered solid materials were suspended in water and neutralized; then the pH was adjusted to between 11 and 13 with conc. ammonium hydroxide (28-30%). It was necessary to decolorize the solution with activated charcoal because of the dye in the bottle and decomposition of the paper and glue. The obtained clear light-colored solution was then acidified with conc. sulfuric acid (diluted sulfuric acid is preferred if large enough equipment is available). The precipitated TPA was filtered, washed free of ammonium sulfate with cold water to neutral pH, then dried at 105° C. 76.4 g of dried TPA was obtained, corresponding to a 76.4% yield.

Note: All yields were based on the actual weight of the scrap material but the yield was actually much higher, considering that the available TPA from the polyester polymer is equal to or around 85.6% or less because of the presence of impurities.

The quality of the recovered TPA was checked by infrared spectrophotometer or by titration against pure analytical grade TPA.

Regardless of the type of scrap material and the method used, the purity of the recovered TPA was always better than 99%. The yields clearly indicate the capability, simplicity and adaptability of the process.

It should be understood that the use of a filter to separate solids from liquids in the above examples is only illustrative. Decantation or centrifugation may also be used.

Waste Disposal

After depolymerization, the formed ethylene glycol can be simply decomposed with activated sludge to form water and $CO_2$. The excess acid part can be neutralized completely. These techniques are well-known in the art.

I claim:

1. A method for the recovery of purified terephthalic acid from terephthalate polyester scrap substantially free of metals, said method comprising the steps of:
   (a) dissolving the polyester in a mixture of sulfuric acid and water in a volume ratio of 8.5–13 to 2 for a period of up to 30 minutes to form a precipitate of crude terephthalic acid;
   (b) diluting the reaction mixture from step (a) with at least an equal volume of water and separating the crude terephthalic acid;
   (c) treating the crude terephthalic acid from step (b) with water and a base selected from the group consisting of potassium hydroxide, sodium hydroxide and ammonium hydroxide to form a solution of a water-soluble salt of the acid;
   (d) filtering the solution from step (c) to remove solid impurities;
   (e) acidifying the filtrate from step (d) with acid to form a precipitate of purified terephthalic acid;
   (f) separating the purified terephthalic acid from step (e); and
   (g) washing the terephthalic acid from step (f) until it is acid- and salt-free.

2. The method according to claim 1, wherein step (a) is carried out at room temperature and atmospheric pressure.

3. The method according to claim 1, wherein said ratio is 11 to 2.

4. The method according to claim 1, wherein sufficient base is added in step (c) to obtain a pH of 6 to 13.

5. The method according to claim 4, wherein the pH is 11.

6. The method according to claim 4, wherein sufficient acid is added in step (e) to obtain a pH of 0–3.

7. The method according to any one of claims 1, 4 and 6, wherein the polyester scrap is in the form of a film from which silver has previously been removed.

8. The method according to any one of claims 1, 4 and 6, wherein the polyester scrap is in the form of a film which includes 0 to 10% by weight of paper, acetate, or vinylidene chloride as impurities.

9. The method according to any one of claims 1, 4 and 6, wherein the polyester scrap is in the form of yarn or textile material.

10. The method according to any one of claims 1, 4 and 6, wherein the polyester scrap is in the form of bottles.

11. A method for liquefying terephthalate polyester scrap, said method comprising the step of dissolving the polyester in a mixture of sulfuric acid and water in a volume ratio of 8.5–13 to 2 to effect depolymerization of the polyester to form terephthalic acid and ethylene glycol.

* * * * *